United States Patent [19]

Klose et al.

[11] 4,101,381

[45] Jul. 18, 1978

[54] METHOD AND REAGENT FOR THE DETERMINATION OF SUBSTANCES FORMING HYDROGEN PEROXIDE

[75] Inventors: Sigmar Klose, Berg; Ulfert Deneke, Peissenberg; Erich Haid, Weilheim; Gunter Weimann, Tutzing, all of Germany

[73] Assignee: Boehringer Mannheim GmbH, Mannheim-Waldhorf, Germany

[21] Appl. No.: 754,878

[22] Filed: Dec. 27, 1976

[30] Foreign Application Priority Data

Aug. 1, 1976 [DE] Fed. Rep. of Germany ....... 2600526

[51] Int. Cl.$^2$ ..................... G01N 33/00; G01N 31/14
[52] U.S. Cl. ............................... 195/99; 195/103.5 C; 195/103.5 R; 195/103.5 UR
[58] Field of Search ................. 195/103.5 C, 103.5 R, 195/103.5 U, 99

[56] References Cited

U.S. PATENT DOCUMENTS

| 3,886,045 | 5/1975 | Meiattini | 195/103.5 C |
| 3,979,262 | 9/1976 | Hunziker | 195/103.5 R |

FOREIGN PATENT DOCUMENTS 2,198,642  3/1974  France.

*Primary Examiner*—Joseph M. Golian
*Assistant Examiner*—C. A. Fan
*Attorney, Agent, or Firm*—Burgess, Dinklage & Sprung

[57] ABSTRACT

In a conventional method for the quantitative determination of substances, particularly in serum, which, by action of an oxidase thereon, combine with oxygen to form hydrogen peroxide and wherein the hydrogen peroxide formed is converted, in the presence of methanol and catalase, to formaldehyde, the formaldehyde is reacted with hydrazone in the presence of ferric chloride, and the dye thus formed is determined photometrically, the improvement comprising using as the hydrazone, 3-methyl-2-sulfonylbenzothiazolone-hydrazone; use of this hydrazone results in the formation of a very easily soluble dye and is suited for use in automatic analyzers.

14 Claims, No Drawings

METHOD AND REAGENT FOR THE DETERMINATION OF SUBSTANCES FORMING HYDROGEN PEROXIDE

The invention relates to a method for determining substances which form hydrogen peroxide with oxygen in the presence of an oxidase. More specifically, the invention relates to a method for the quantitative determination of substances, particularly in serum, which, by action of an oxidase thereon, combine with oxygen to form hydrogen peroxide, and wherein the hydrogen peroxide that is formed is converted in the presence of methanol and catalase to formaldehyde, the formaldehyde is reacted with a hydrazone in the presence of ferric chloride, and the dye thus formed is determined photometrically.

French Pat. No. 2,198,642 discloses a method for the determination of uric acid by reaction with uricase to form hydrogen peroxide, reaction of the hydrogen peroxide with catalase and methanol to form formaldehyde, and reaction of the formaldehyde with 3-methylbenzothiazolonehydrazone and ferric chloride to form a dye which can be determined photometrically. A similar method has been published in Chem. Pharm. Bull. 17, 1304–1305 (1969) for the determination of glucose by the use of glucose oxidase. One advantage of this method is its relatively low susceptibility to interference from medicaments and other foreign substances. A considerable disadvantage, however, is the low stability of 3-methylbenzothiazolonehydrazone (MBTH) and the relatively poor water solubility of the dye formed in the color reaction. This leads to relatively great carry over between the individual determinations, so that the method is poorly suited expecially for use in continuous flow automatic analyzers. This effect is amplified, since in the oxidation procedure necessary for the development of the color, secondary reactions occur in which an insoluble product is formed. In automatic analyzers this product becomes deposited in the tubes, and glass spirals, and thus further increases the carry over. Furthermore, this leads to an unstable, i.e., drifting base line.

In order for this known method to be used despite these disadvantages, the analysis time must be considerably lengthened, and a relatively frequent washing of the apparatus must be performed. Lastly, allowance must be made for the drifting of the base line.

The invention substantially eliminates the above-described disadvantages in the conventional determination methods.

In accordance with the invention, in a method for the quantitative determination of substances in the serum which combine with oxygen under the action of oxidase to form hydrogen peroxide whereby, the hydrogen peroxide that is formed in converted in the presence of methanol and catalase to formaldehyde, the latter is reacted with a hydrazone in the presence of an oxidizing agent, and the dye thus formed is photometrically determined, an improvement is provided in that 3-methyl-2-(sulfonyl)-benzothiazolonehydrazone (SMBTH) is used as the hydrazone.

Surprisingly, in the method of the invention a very easily soluble dye is formed, so that the above-described difficulties, which are to be attributed to the insolubility of the oxidation product that develops in the formation of the dye, no longer occur. This is surprising, since MBTH itself has good solubility in an aqueous medium (4.8 grams per 100 milliliters at pH 1) and is unobjectionable in this regard, while the MBTH sulfonate used in accordance with the invention has a far poorer solubility than MBTH, namely 0.6 g/100 ml at pH 1, so that a still further reduced solubility was to be expected also of the oxidation product formed, and a correspondingly poorer usefulness in this kind of procedure.

The method of the invention can be used in principle for all determinations in which hydrogen peroxide is formed. The formation of hydrogen peroxide in enzymatic catalysis is brought about by oxidases, so that the method is generally suitable for the determination of all substrates of oxidases. The term "oxidases", as used herein, is to be understood to mean those enzymes which are capable of oxidizing their substrate with molecular oxygen to form hydrogen peroxide. Typical examples of such oxidases are uricase, glucoseoxidase and cholesteroloxidase. The corresponding substrates are uric acid, glucose and cholesterol, respectively.

The method can be practiced under the conditions set forth in the publications mentioned in the beginning. The reaction of the substance being determined with the corresponding oxidase, such as uricase, cholesteroloxidase or glucoseoxidase, is performed in the manner well known to the technician of the art. The hydrogen peroxide that is formed is reacted with methanol and catalase to form formaldehyde and water. The technician is also familiar with this reaction so that it need not here be further described. The formaldehyde that is formed is then reacted with MBTH sulfonate in the presence of an oxidizer, to form a dye having a $\lambda_{max}$ at 620 and one at 670 nm, $\epsilon \sim 60,000$.

The dye forming reaction is given by the following equation:

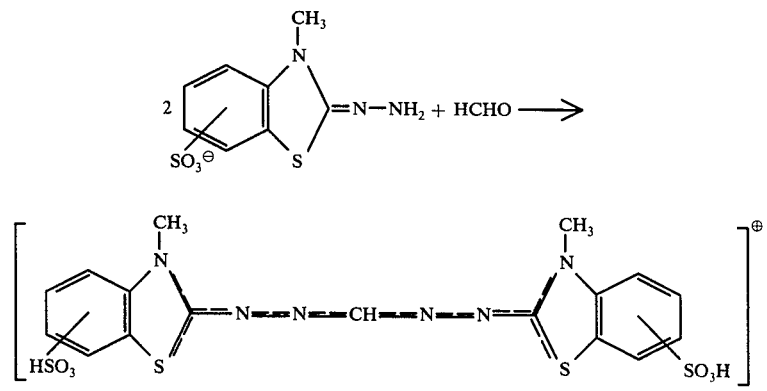

Examples of oxidizers which are particularly suitable within the scope of the invention are potassium cyanoferrate(III), $FeCl_3$ or $(NH_4)_4Ce(SO_4)_4$. Preferably these oxidizers are used in the form of a 0.2 to 5% solution in dilute acid, especially in sulfuric acid. In the selection of the solvent it is to be noted that the extinction coefficient of the dye that is formed depends on the pH value, and is strongest in an acid medium at pH values under 3. Preferably, therefore, the procedure is performed between pH 0.5 and 3. To attain this pH value it is best to use strong mineral acids, such as sulfuric acid, hydrochloric acid, phosphoric acid, nitric acid and the like.

Additional subject matter of the invention is a reagent for the quantitative determination of substances in the serum which under the action of oxidase react with oxygen to form hydrogen peroxide, the said reagent containing an oxidase, catalase, methanol, buffer, an oxidizer and an acid, and being characterized by a content of 3-methyl-2-(sulfonyl)-benzothiazolonehydrazone.

The reagent can be in dry form or in a solution. The buffer substance that is used in each case is governed by the enzyme that is used, and is prepared for the most suitable pH value. The expert is familiar with the selection and preparation of such buffers. For example, in the use of uricase with catalase, pH values between about 7 and 9, preferably between 8.0 and 8.6, are suitable. Borate buffer is preferred. In the case of cholesteroloxidase and catalase pH values between 6.0 and 8.5, preferably between 6.5 and 7.5, are suitable. In this case phosphate buffer is preferred.

The methanol concentration is to be about 2 to 8% by volume. However, higher or lower concentrations may be suitable. Examples of reagents of the invention are as follows:

Reagent A:
  more than 0.1 U/ml of uricase
  more than 800 U/ml of catalase
  0.02–0.01 M buffer pH 7–9
  2–8 vol. % of methanol 0.01–0.1% of a non-ionic surface active agent, and separately therefrom
  0.03–0.5% of 3-methyl-2-(sulfonyl)benzothiazolonehydrazone
  0.3–3% potassium cyanoferrate III in dilute sulfuric acid.

Reagent B:
  more than 0.05 U/ml of cholesteroloxidase
  more than 0.05 U/ml of cholesterolesterase
  more than 800 U/ml of catalase
  0.2–1.0 M of buffer pH 6.0–8.5
  2–8 vol. % of methanol
  0.1–0.8% of non-ionic surface active agent and separately therefrom
  0.03–0.5% of 3-methyl-2-(sulfonyl)-benzothiazolonehydrazone
  0.5–3.0% of $FeCl_3$ in dilute sulfuric acid.

EXAMPLES

The following examples further illustrate the invention.

(A) Preparation of the hydrazone used pursuant to the invention 1000 ml of fuming sulfuric acid having a sulfur trioxide content of at least 65% is slowly added, with stirring and cooling with ice to 1,580 ml of sulfuric acid of high purity (95–98%). The mixture obtained is cooled to 0° to 5° C and 500 g of N-methylbenzothiazolonehydrazone hydrochloride (MBTH . HCl) is added portionwise. Care is taken to see that the temperature does not exceed 10 to 13° C. The addition is completed in one hour. Then the mixture is stirred for 1½ hours at about +10° C, until the solution has become completely clear with a light yellow tint.

The solution is carefully poured onto 20 liters of ice and the temperature is lowered to 0° C. by the addition of more ice. After two hours of standing, the crystals that have formed are suction filtered and washed with cold, distilled water, and this washing is repeated until the wash water is free of sulfate.

For the recrystallization of the free acid the still moist substance is suspended in about 4 liters of distilled water and, with vigorous stirring, is brought to a pH of 8.0 with about 400 ml of freshly prepared 30% KOH, whereupon the entire precipitate passes into solution. The solution is then clarified through a filter aid (crystal theorite) and acidified with 10N sulfuric acid to pH 1.5 with thorough stirring. The precipitate is let stand for one hour, suction filtered, and, as described above, washed acid-free. Then it is dried in vacuo at 40° C over $CaCl_2$. Yield: 500 to 540 g.

For the preparation of the potassium salt, the acid thus obtained is suspended in 1.5 liters of hot water and with about 400 ml of freshly prepared 30% KOH it is brought to a pH of 8. The solution is heated at 80° C, and about 4 liters of isopropanol at boiling temperature are added, with stirring, until a slight turbidity occurs. Then the mixture is cooled in the ice bath and brought to crystallization at −20° C. The crystallizate is suction filtered, washed with methanol and again vacuum dried at elevated temperature over $CaCl_2$ until its weight is constant. Yield: 500 to 520 g of potassium salt (72–75% of the theory).

EXAMPLE 1

Determination of Uric Acid

The reaction takes place in accordance with the following equations:
I. Uric acid + $O_2$ $\xrightarrow{uricase}$ allantoin + $H_2O_2$
II. $H_2O_2$ + $CH_3OH$ $\xrightarrow{catalase}$ HCHO + 2 $H_2O$
III. HCHO + 2 SMBTH $\xrightarrow{oxidizer}$ dye.

Regents

1. Enzyme reagent:
  Uricase >0.12 U/ml
  Catalase >900 U/ml
  0.05 M borate buffer pH 8.3
  4% (by volume) of methanol
  0.04% hydroxypolyethoxydodecane
2. Chromogen reagent:
  0.1% solution of SMBTH in water
3. Oxidation reagent:
  1% solution of potassium cyanoferrate(III) in 0.45N sulfuric acid.

The determination is performed on a Technicon "Auto-Analyzer" ® in the following manner. By means of a peristaltic pump, 1 ml of enzyme reagent per minute is pumped into a flow system. By means of the same pump, 0.1 ml per minute of the uric acid specimen is pumped into the reagent. The mixture, which by means of a suitable apparatus has been segmented by air bubbles, then flows through a glass spiral of 20 turns. Here reactions I and II take place. Then the mixture goes to a dialyzer. This dialyzer, through which the mixture flows continuously, is such that two streams can flow through it, separated only by a semipermeable membrane. Molecules of a molecular weight under about 600 dialyze out of the mixture described above into a receiving solution which consists of the chromogen reagent, which in turn is pumped by the same peristaltic pump. The pumping rate is 1.0 ml/min. This flow, too, is segmented by air bubbles by means of a suitable apparatus.

The formaldehyde dialyzed into the receiving solution is reacted, after the oxidation reagent has been pumped into it at a pumping rate of 0.23 ml/min, to form the previously described dye as it flows through additional glass coils. Its extinction is measured at 620 or 670 nm in a suitable photometer equipped with a flow-through cell (after removal of the air bubbles). After calibration with a uric acid standard of known concentration, the uric acid concentrations in unknown specimens can be determined by this method. If the appartus is connected to a sampler, it is possible to determine 60 different specimens per hour.

The coefficient of variation in a multiple determination of the same specimen is 1%. There is a linear relationship between the extinction and the uric acid concentration up to 20 mg per 100 ml of specimen solution, and this covers the entire range involved in clinical diagnosis.

If a comparison is made with a method of determining uric acid in the serum which is recognized as reliable (N. Kageyama, Clin. Chim. Acta 31 (1971) 421 and H. Mathies et al., Med. Clin. 69 (1974) 607), one obtains a straightline correlation of the equation $y = 0.98x + 0.3$, with a correlation coefficient of 0.993. The values $\int x$ represent the method used for comparison, the $y$ values the method described above. The result proves very good correlation.

EXAMPLE 2

Cholesterol Determination

Depending on whether free cholesterol or cholesterol ester is to be determined, the determination is made in accordance with the following Equations I*a* and I*b*, in conjunction with Equations II and III of Example 1.

I*a* 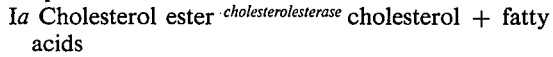 Cholesterol ester $\xrightarrow{cholesterolesterase}$ cholesterol + fatty acids I*b* 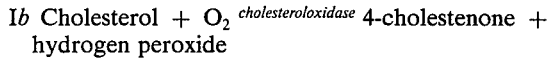 Cholesterol + $O_2$ $\xrightarrow{cholesteroloxidase}$ 4-cholestenone + hydrogen peroxide

Reagents

1. Enzyme reagent:
   Cholesteroloxidase >0.07 U/ml
   Cholesterolesterase >0.07 U/ml
   Catalase 900 U/ml
   0.4 M phosphate buffer pH 7.0
   4% (v/v) methanol
   0.3% hydroxypolyethoxydodecane
2. Chromogen reagent:
   0.1% solution of SMBTH in water
3. Oxidation reagent:
   1% solution of ferric chloride in 0.45 N sulfuric acid.

The apparatus is substantially the same as that described in Example 1, the only difference being that, after the specimen and the enzyme reagent have been mixed together, the solution passes through a heating bath of 37.5° C. Here reactions I*a* and I*b* and II take place. The procedures that follow are the same as in the uric acid determination of Example 1. In the performance of the analyses the specimens have to be diluted 1 : 25 beforehand, since otherwise excessively high extinctions would be obtained.

The range of the linear relationship between the extinction and the cholesterol concentration extends up to 600 mg of cholesterol in 100 ml of specimen (serum).

The variation coefficient in the case of multiple determinations of the same specimen is 1%.

A methodological comparison with a reference method considered correct and reliable (P. Roeschlau et al, Z. Clin. Chem. Clin. Biochem. 12 (1974) 226) shows a straightline correlation of the equation $y = 0.98x + 5.4$ with a correlation coefficient of 0.99. The $x$ values represent the method used for comparison and the $y$ values the method described. The correlation proves a very good agreement between the two methods.

It will be understood that the specification and examples are illustrative but not limitative of the present invention and that other embodiments within the spirit and scope of the invention will suggest themselves to those skilled in the art.

What is claimed is:

1. Method for the quantitative determination of a substance which forms $H_2O_2$ with oxygen under the action of an oxidase, which comprises treating the $H_2O_2$ formed with methanol and catalase to yield formaldehyde, reacting the formaldehyde with 3-methyl-2-(sulfonyl)-benzothiazolone-hydrazone in the presence of an oxidizer, and photometrically determining the dye formed thereby as a measure of the said substance initially present.

2. Method as claimed in claim 1 wherein uric acid is determined and the said oxidase is uricase.

3. Method as claimed in claim 1 wherein glucose is determined and the said oxidase is glucose oxidase.

4. Method as claimed in claim 1 wherein cholesterol is determined and said oxidase is cholesterol oxidase.

5. Method as claimed in claim 1 wherein the oxidizer is potassium cyanoferrate (III).

6. Method as claimed in claim 1 wherein the oxidizer is $FeCl_3$.

7. Method as claimed in claim 1 wherein the oxidizer is $(NH_4)_4\text{-}Ce(SO_4)_4$.

8. Method as claimed in claim 1 wherein said oxidizer is used in the form of a 0.2 to 5% solution thereof in a dilute acid.

9. Method as claimed in claim 1 wherein the said dye is formed at a pH value of between 0.5 and 3.

10. Reagent for the quantitative determination of substances in the serum which form $H_2O_2$ with oxygen under the action of oxidase, containing an oxidase, catalase, methanol, buffer, an oxidizer and acid, characterized by a content of 3-methyl-2-(sulfonyl)-benzothiazolonehydrazone.

11. Reagent for the determination of uric acid, characterized in that it contains
   more than 0.1 U/ml of uricase,
   more than 800 U/ml of catalase,
   0.02 – 0.1 M buffer pH 7 – 9,
   2–8 vol. % of methanol,
   0.01–0.1% of a non-ionic surface active agent, and separately therefrom
   0.03 – 0.5% of 3-methyl-2-(sulfonyl)-benzothiazolonehydrazone,
   0.3 – 3% of potassium cyanoferrate III in dilute sulfuric acid.

12. Reagent as claimd in claim 11 characterized in that it contains more than 0.05 U/ml of cholesteroloxidase,
more than 0.05 U/ml of cholesterolesterase,
more than 800 U/ml of catalase,
0.2 – 1.0 M of buffer pH 6.0 – 8.5,
2 – 8 vol. % of methanol,
0.1 – 0.8% of non-ionic surface active agent and separately therefrom
0.03 – ≡% of 3-methyl-2-(sulfonyl)-benzothiazolonehydrazone,
0.5 – 3.0% of $FeCl_3$ in dilute sulfuric acid.

13. Reagent as claimed in claim 11, characterized in that it contains, as the buffer, borate buffer pH 8.0 to 8.6.

14. Reagent as claimed in claim 12, characterized in that, as the buffer, it contains phosphate buffer pH 6.5 to 7.5.

* * * * *

UNITED STATES PATENT AND TRADEMARK OFFICE
CERTIFICATE OF CORRECTION

PATENT NO. : 4,101,381
DATED : July 18, 1978
INVENTOR(S) : Sigmar Klose; Ulfert Deneke; Erich Haid and Gunter Weimann It is certified that error appears in the above-identified patent and that said Letters Patent are hereby corrected as shown below:

Cover page at [30], the Priority Data,

"Aug. 1, 1976" should read --Jan. 8, 1976--

Signed and Sealed this

Fifteenth Day of May 1979

[SEAL]

Attest:

RUTH C. MASON
Attesting Officer

DONALD W. BANNER
Commissioner of Patents and Trademarks